United States Patent [19]
Toole et al.

[11] Patent Number: 5,902,795
[45] Date of Patent: May 11, 1999

[54] OLIGOSACCHARIDES REACTIVE WITH HYALURONAN-BINDING PROTEIN AND THEIR METHODS OF USE

[75] Inventors: Bryan P. Toole, Watertown; Shib D. Banerjee, Melrose, both of Mass.

[73] Assignee: Trustees of Tufts College, Medford, Mass.

[21] Appl. No.: 08/306,150

[22] Filed: Sep. 14, 1994

Related U.S. Application Data

[63] Continuation-in-part of application No. 07/899,249, Jun. 16, 1992, abandoned.

[51] Int. Cl.$^6$ .................................................. A61K 31/715
[52] U.S. Cl. .................................... 514/54; 514/2; 514/4; 514/61
[58] Field of Search .................................. 514/54, 61, 2, 514/4

[56] References Cited

FOREIGN PATENT DOCUMENTS

WO94/20115  9/1994  WIPO.

OTHER PUBLICATIONS

Wasteson et al. *Int. J. Cancer* 1973, 12, 169–178.
Yu et al. *Deveopmental Dynamics* 1992, 193(2), 145–151.
Hardwick, C. et al., "Molecular Cloning of a Novel Hyaluronan Receptor that Mediates Tumor Cell Motility," *Journal of Cell Biology*, 117 (6) :1343–1350 (1992).
Folkman, Judah and Shing Yuen, "Angiogenesis," *Journal of Biological Chemistry*, 267 (16) :10931–10934 (1992).
Kundson W. and Knudson C., "Assembly of a Chondrocyte–Like Pericellular Matrix on Non–Chondrogenic Cells," *Journal of Cell Science*, 99:227–235 (1991).
Toole, B. et al., "Hyaluronan–Cell Interactions in Limb Development," *Developmental Patterning of the Vertebrate Limb*, 215–223 (1991). Edited by J.R. Hinchliffe et al., Plenum Press, New York.
Toole, B.P., "Proteoglycans and Hyaluronan in Morphogenesis and Differentiation," Chapter 9 *Cell Biology of Extracellular Matrix*, pp.: 305–341, Second Edition, edited by Elizabeth D. Hay, Plenum Press, New York (1991).
Auerbach, R. et al., "Assays for Angiogenesis: A Review," *Pharmac. Ther.*, 51:1–11 (1991).
Toole, B.P., "Hyaluronan and its Binding Proteins, the Hyaladherins," *Current Biology, Ltd.*, ISSN 0955–0674, 839–844 (1990).
West, D.C. and Kumar, S., "The Effect of Hyaluronate and Its Oligosaccharides on Endothelial Cell Proliferation and Monolayer Integrity," *Experimental Cell Research*, 183:179–196 (1989).
West, D.C. et al., "Angiogenesis Induced by Degradation Products of Hyaluronic Acid," *Science*, 228:1324–1326 (1985).
Banerjee, S. and Toole, B., "Monoclonal Antibody to Chick Embryo Hyaluronan–Binding Protein: Changes in Distribution of Binding Protein during Early Brain Development," *Developmental Biology*, 146:186–197 (1991).
Turley, E. and Moore, D., "Hyaluronate Binding Proteins Also Bind to Fibronectin, Laminin and Collagen," *Biochemical and Biophysical Research Communications*, 121(3) :808–814 (1984).
Turley, E.A. and Torrance, J. et al. "Localization of Hyaluronate and Hyaluronate–binding Protein on Motile and Non–motile Fibroblasts," *Exp. Cell Research* 161:17–28 (1984).
American Type Culture Collection (ATCC) Catalogue of Cell Lines & Hybridomas, 7th ed. (1992), pp. 55 and 147.
Harlow, Ed. et al. "Antibodies A Laboratory Manual," Cold Spring Harbor Press, Cold Spring Harbor, NY, pp. 321–358 (1988).
Waldman, Thomas A., "Monoclonal Antibodies in Diagnosis and Therapy," *Science* 252:1657–1662 (1991).
Dillman, R.O., *An. Int. Med.* 111:592–603 (1989).
Turley, E.A. et al., "Characterization and Hyaluronate Binding Proteins Isolated from 3T3 and Murine Sarcoma Virus Transformed 3T3 Cells," *Biochemistry* 26:2997–3005 (1987).
Boudreau, Nancy et al., "Fibronectin, Hyaluronan, and a Hyaluronan Binding Protein Contribute to Increased Ductus Arteriosus Smooth Muscle Cell Migration," *Dev. Biol.* 143:235–247 (1991).
Goding, James W. "Monoclonal Antibodies: Principles and Practice," *Academic Press*, London, pp. 56–91 (1983).
Babu, Ramesh et al., "Elevated Level of Hyaluronic Acid Binding Protein in Diabetic Rats," *Biochem. Int'l* 22 (5):877–886 (1990).
Turner, R.E. et al., "Role of Hyaluronan–Binding Protein in Chondrogenesis," *J. Cell Biol.* 115 (3, part 2) :447a (Abstract #2598) (1991).

*Primary Examiner*—Kathleen K. Fonda
*Attorney, Agent, or Firm*—Hamilton, Brook, Smith & Reynolds, P.C.

[57] ABSTRACT

Hyaluronan-binding protein (HABP) is expressed on the cell surface during tumor cell and endothelial cell migration and during capillary-like tubule formation. Monoclonal antibodies and hyaluronan oligosaccharides are described which specifically recognize HABP and can be used to (1) inhibit tumor growth by preventing tumor vascularization, (2) inhibit tumor cell migration and (3) image tumors.

41 Claims, 10 Drawing Sheets

FIG.4A
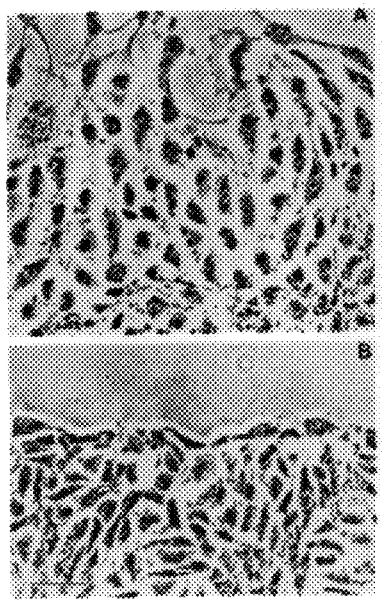
FIG.4B
FIG.4C
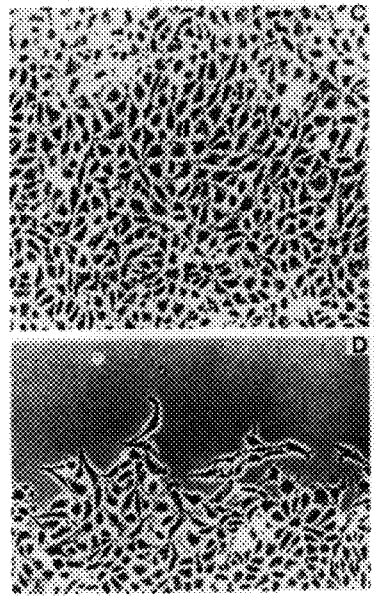
FIG.4D

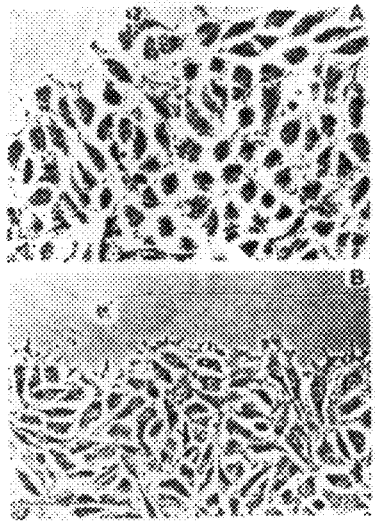# 
FIG.5A
FIG.5B
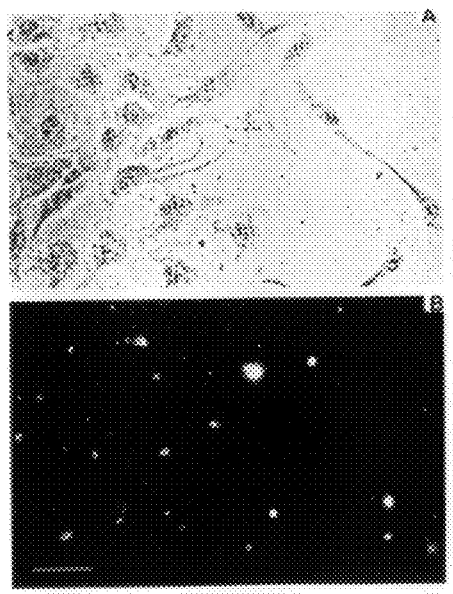
FIG.6A
FIG.6B

OLIGOSACCHARIDES REACTIVE WITH HYALURONAN-BINDING PROTEIN AND THEIR METHODS OF USE

RELATED APPLICATIONS

This application is a Continuation-in-Part of U.S. application Ser. No. 07/899,249, filed Jun. 16, 1992, now abandoned, which is incorporated herein by reference.

GOVERNMENT SUPPORT

Work described herein was supported in part by National Institutes of Health Grants HD 23681 and DE 05838.

BACKGROUND OF THE INVENTION

The extracellular matrix plays an important role in tissue structure and in cell behavior, function and differentiation. Many of the effects of matrix macromolecules are mediated by binding sites or receptors on the cell surface. Endothelial cell morphogenesis, as occurs in angiogenesis or embryonic vasculogenesis, involves a series of events that include cell migration, tubule formation, and division. Folkman, J. and Haudenschild, C. *Nature,* 288:551–556 (1980); Poole, T. and Coffin, J. *J. Exp. Zool.,* 251:224–231 (1989). Many experimental studies have indicated that the interaction of endothelial cells with the extracellular matrix plays a key role in these processes. Madri, J. and Pratt, B. *J. Histochem. Cytochem.,* 34:85–91 (1986); Furcht, L. *Lab. Invest.,* 55:505–509 (1986); Ingber, D. *J. Cell. Biochem.,* 47:236–241 (1991). For example, the integrin family of matrix receptors and a 67–69 kilodalton (kDa) laminin receptor appear to mediate at least part of this influence of matrix on the behavior of endothelial cells. Charo et al., *J. biol. Chem.,* 262:9935–9938 (1987); Dejana et al., *J. Cell Biol.,* 107:1215–1223 (1988); Grant et al., *Cell,* 58:933–943 (1989); Basson et al., *Dev. Biol.,* 146:186–197 (1990); Defilippi et al., *J. Cell biol.,* 114:855–863 (1991).

Hyaluronan is a high molecular weight, highly anionic polysaccharide found in the extracellular matrix and at cell surfaces. It is composed of 200–10,000 disaccharides of B-1,4-glucuronate-B-1,3-N-acetylglucosamine, and has a molecular weight in the range of from about $6 \times 10^4$ to about $1.2 \times 10^7$. Hyaluronan is a major component of matrices in which cells proliferate and migrate during embryonic morphogenesis and differentiation, tissue regeneration, tissue healing, tissue remodeling and tumorigenesis. See Toole, B., *Cell Biology of Extracellular Matrix* (F. Hay, ed.) pp. 259–294 (1981).

The pericellular region surrounding migrating tips of newly forming capillaries is enriched in hyaluronan. Ausprunk et al., *Am. J. Pathol.,* 103:367–375 (1981). It has also been shown that capillaries of the chorioallantoic membrane begin to form in hyaluronan-rich areas but the level of hyaluronan surrounding the capillaries rapidly decreases thereafter. Ausprunk et al., *Am. J. Pathol.,* 103:367–375 (1981); Ausprunk, D., *Am. J. Anat.,* 177:313–331 (1986). Other investigations have shown that blood vessel formation does not occur in hyaluronan-rich zones and that endothelial cell growth is inhibited by polymeric hyaluronan. Feinberg, R. and Beebe, B., *Science,* 220:1177–1179 (1983); West, D. and Kumar, S., *Exp. Cell Res.,* 183:179–196 (1989). However, oligosaccharides of hyaluronan containing 3–16 disaccharide repeats have been shown to stimulate blood vessel formation and endothelial cell growth. West, et al., *Science,* 228:1324–1326 (1985); West, D. and Kumar, S., *Exp. Cell Res.,* 183:179–196 (1989).

SUMMARY OF THE INVENTION

This invention pertains to methods of detecting and treating tumors and angiogenesis in disease states by exploiting the association of hyaluronan binding proteins (HABPs) with tumor vascularization and with tumor cells themselves. This invention is based on the discovery that HABP is expressed on the cell surface during cell migration and capillary-like tubule formation, both of which occur during the vascularization of a tumor.

The association between HABP expression and tumor vascularization and tumor cell migration provides a basis for using compounds to block and thus treat tumor growth and metastasis.

Additionally, this association provides a basis for using compounds that can bind to the HABPs, and thus, if appropriately labeled, can detect the presence of the HABPs which indicate the vascularization and malignancy of a tumor.

This invention is therefore directed to compounds which can detect and treat tumorigenesis, tumor metastasis and angiogenesis in disease states. The compounds which can be used in this invention include both hyaluronan (HA) oligosaccharides and antibodies which are specific for HABPs.

HA oligosaccharides of this invention recognize HABP present in tissues and inhibit cell migration and formation of capillary-like tubules. As used herein, HA oligosaccharides include compounds containing one or more repeating units of B-1,4-glucuronate-B-1,3-N-acetylglucosamine which are capable of binding specifically to a HABPs and inhibiting angiogenesis and tumor metastasis. The HA oligosaccharides of this invention also include oligosaccharides which are derivatives or modifications of the HA oligosaccharides which are able to bind to HABPs and inhibit angiogenesis and tumor metastasis.

Further, the inventors have discovered that the interaction of endogenous hyaluronan with endothelial cells is essential to endothelial morphogenesis, rather than antagonistic as suggested by the literature. These apparently contradictory results are due to the opposing effects of low versus high concentrations of endogenous hyaluronan in the pericellular milieu of the endothelial cell.

Based on this discovery, this invention is directed to antibodies specific against HABPs. The antibodies of this invention are capable of blocking hyaluronan binding to soluble and cell surface-bound HABP and inhibiting the formation of hyaluronan-dependent pericellular matrices. In the preferred embodiment, a monoclonal antibody, MAb IVd4, has been raised that recognizes HABP present in many embryonic and tumor cells and on the surface of cultured cells from a variety of species. The use of MAb IVd4 blocks hyaluronan binding to soluble and cell surface-bound HABP and inhibits the formation of HA-dependent pericellular matrices.

In one embodiment of this invention, the monoclonal antibody is used as a treatment for tumors or angiogenesis in disease states by passive immunotherapy, or as a targeting agent for selective delivery of either cytotoxic agents, cytokines or other therapeutic agents to a tumor or other disease site(s). In passive immunotherapy, a physiologically-acceptable solution of the monoclonal antibody is administered to the afflicted mammal by injection into a blood vessel or by direct application to a surgical site using a biocompatible gel, film or sponge. The monoclonal antibody inhibits migration of endothelial cells, capillary-like tubule formation, and tumor cell migration by reducing HA-HABP interactions. When used as a targeting agent, the monoclonal antibody is coupled or conjugated to either a therapeutic agent, a cytotoxic agent or a cytokine.

In another embodiment, HA oligosaccharides are used to treat tumors or angiogenesis in disease states by passive therapy. In passive therapy, the HA oligosaccharide is admixed with a physiologically-acceptable carrier and administered into a vein, artery, or the spinal fluid. The HA oligosaccharide composition can also be directly introduced into a surgical site using a biocompatible gel, film or sponge. The introduction of the HA oligosaccharide composition into the body of a mammal afflicted with a tumor will cause a reduction in the level of HABPs on the cell surface. A reduction in the level of HABPs necessarily results in a decrease in HA-HABP interactions. As a result, endothelial cell migration, capillary-like tubule formation, and tumor cell migration are inhibited.

The HA oligosaccharides can also be used as targeting agents for selective delivery of anti-tumor or anti-angiogenesis agents to a tumor or other site of angiogenesis. When used as a targeting agent, the HA oligosaccharides are coupled or conjugated to either a cytotoxic agent, a cytokine or some other therapeutic.

In yet another embodiment of this invention, a monoclonal antibody or an HA oligosaccharide is used to image tumors in vivo by conjugating the monoclonal antibody or HA oligosaccharide to a detectable label. The antibody or oligosaccharide composition is then administered to a mammal suspected of having a tumor. The signal generated by the label is detected by a photoscanning device. The detected signal is then converted to an image of the tumor.

The HA oligosaccharides that are preferred for use in both therapeutic and diagnostic applications are those having between one disaccharide unit and 16 repeating disaccharide units. It is even more preferable to use HA oligosaccharides having between three repeating disaccharide units (hexasaccharide) and seven repeating disaccharide units (tetradecasaccharide).

These and other aspects, objects and advantages of the present invention will become apparent from the following detailed description, particularly when taken in conjunction with the accompanying drawings.

BRIEF DESCRIPTION OF THE DRAWINGS

FIGS. 4A through 4D are micrographs showing confluent monolayers of bovine aortic endothelial cells that were wounded by scratching with a smoothened pasteur pipette and then incubated in the presence (FIGS. 4B and 4D) or absence (FIGS. 4A and 4C) of MAb IVd4.

FIG. 5A is a micrograph showing a confluent monolayer of bovine aortic endothelial cells wounded by scratching with a smoothened pasteur pipette and then incubated in the absence of HA oligosaccharide.

FIG. 5B is a micrograph showing a confluent monolayer of bovine aortic endothelial cells wounded by scratching with a smoothened pasteur pipette and incubated in the presence of HA hexasaccharide.

FIG. 6A is a micrograph showing a confluent monolayer of pulmonary artery endothelial cells wounded by scratching with a smoothened pasteur pipette and then incubated with HA hexasaccharide.

FIG. 6B is a micrograph showing absence of immunoreactivity of MAb IVd4 when the artery endothelial cells shown in FIG. 6A have been incubated with HA hexasaccharide.

DETAILED DESCRIPTION OF THE INVENTION

Figure 1A:
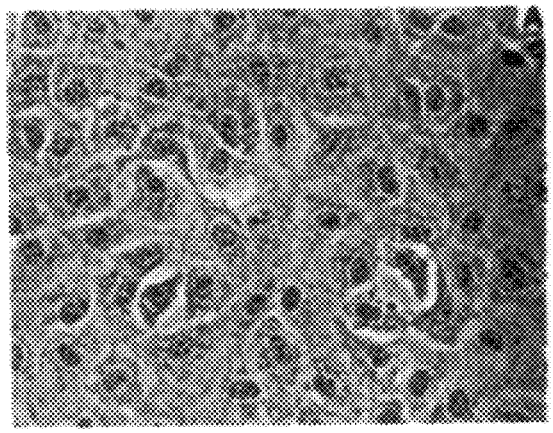
FIG. 1A is a micrograph showing a confluent culture of pulmonary artery endothelial cells under phase contrast.

A monoclonal antibody, MAb IVd4, has been discovered that specifically binds to hyaluronan-binding protein (HABP). MAb IVd4 inhibits the migration of cells from a confluent monolayer after wounding of the monolayer. It has also been discovered that HA oligosaccharides inhibit cell migration. In addition, both Mab IVd4 and HA oligosaccharides inhibit the morphogenesis of capillary-like tubules. These relationships can be exploited for diagnosing and treating tumors and angiogenesis in disease states.

Angiogenesis is a complex morphogenic process in which endothelial cells form new capillaries. Tumor growth is dependent on angiogenesis. In one embodiment, this invention is directed to methods of inhibiting tumor growth by inhibiting angiogenesis. The general features of caillary formation can be summarized as follows: (1) new capillaries arise from small venules which lack smooth muscle; (2) in the presence of an angiogenic stimulus, such as a small tumor nidus, endothelial cells within a venule begin to degrade the vascular basement membrane and protrude through the wall of the vessel; (3) the migration of endothelial cells toward the angiogenic stimulus is associated with their linear alignment as they form a capillary sprout; (4) endothelial cell proliferation takes place within the sprout but not usually at its tip; (5) the tip of one sprout fuses with another to form a capillary loop through which blood begins to flow, and new sprouts originate from each loop; and (6) a new basement membrane is formed and microvascular pericytes are incorporated into it. See Folkman, *J. Cancer Res.*, 46:467–473 (1986).

MAb IVd4 inhibits endothelial cell migration and capillary-like tubule formation by reacting with a specific epitope of HABP, and thereby blocking the interaction of endogenous hyaluronan with HABP. MAb IVd4 blocks (1) the binding of exogenous HA to soluble or membrane-bound HABP and (2) the formation of pericellular matrices which are dependent on the endogenous HA-HABP interaction. Several types of cells exhibit pericellular matrices that are dependent on both HA and HABP, and assembly of these matrices is inhibited by HA oligosaccharides (see Knudson, W. and Knudson, C., *J. Cell Sci.*, 99:227–235 (1991)) and MAb IVd4. Although endothelial cells do not normally produce large amounts of HA, they do produce small pericellular matrices that are dependent on HA and HABP. These pericellular matrices play an important role in morphogenetic processes such as those involved in angiogenesis.

High concentrations of HA oligosaccharide cause the disappearance of MAb IVd4 immunoreactivity in the lamellipodia and other areas of the cell membrane of motile endothelial cells. This discovery indicates that treatment of motile endothelial cells with HA oligosaccharides leads to a reduction in the level of membrane-associated HABPs and consequently to a loss of HA-HABP interactions. This absence of immunoreactivity is not the result of the occupation of HABP by the added HA oligosaccharide instead of the antibody because: (1) HA oligosaccharides have a low affinity of binding to HABP and thus are readily removed in the process of washing prior to reaction with antibody, and (2) concomitant with the loss of immunoreactivity in the cell membrane, immunoreactivity persists in the subcellular matrix (See FIG. 6). The treatment of endothelial cells with HA oligosaccharide, therefore, leads to loss of HABP from the cell membrane, and this loss results in an inhibition of cell migration. HA oligosaccharide inhibits capillary-like tubule formation in the same way.

The effect of HA oligosaccharide discussed above demonstrates that membrane-bound HABP is subject to "down-regulation" in a manner similar to that of hormone receptors that are in the presence of excess ligand. See, e.g., Ronnett et al., *J. Biol. Chem.* 258:283–290 (1983). The fact that the subcellular immunoreactivity observed in endothelial cultures is largely attached to the substratum (see below) explains why it is not lost in similar fashion to the membrane HABP when exposed to HA oligosaccharide, since this extracellular HABP would not be subject to the membrane events involved in down-regulation.

Thus, the inventors have shown that the HA-HABP interaction is required for endothelial cell morphogenesis. MAb IVd4 recognizes three proteins, of molecular weight 93, 90 and 69 kDa, in Western blots of partially purified HABP preparations from chick embryo brain. Extracts of endothelial cells also contain the 93 and 69 kDa proteins as well as a major MAb IVd4-reactive protein of approximately 50 kDa. These proteins are not related to the hyaluronate binding protein CD44. Culty et al., *J. Cell Biol.* 111:2765–2774 (1990). However, another HABP, isolated from normal and transformed fibroblasts, is of particular interest since interaction of HA with this protein promotes cell movement and since it is also preferentially located in lamellipodia of motile cells. Turley et al., *J. Cell Sci.*, 78:133–145 (1985); Turley et al., *J. Cell Biol.*, 112:1041–1047 (1991); Boudreau et al., *Der. Biol.*, 143:235–247 (1991); Turley, E. and Torrance, *J. Exp. Cell Res.*, 161:17–28 (1984). This HASP is a complex having a molecular weight of approximately $1 \times 10^6$. Turley, E. and Auersperg, N. *Exp. Cell Res.*, 182:340–348 (1989). Previous studies have shown that low concentrations of HA oligosaccharides are angiogenic, and that this angiogenic effect may derive from the stimulatory effect of the HA oligosaccharide on endothelial cell proliferation. West et al., *Science*, 228:1324–1326 (1985); West, D. and Kumar, S. *Exp. Cell Res.*, 183:179–196 (1989). In contradistinction, the present invention is based on the surprising discovery that high concentrations of HA oligosaccharides inhibit endothelial cell migration and assembly into capillary-like tubules.

The stimulatory effect of low concentrations of HA oligosaccharide on proliferation is not due to competitive-inhibition of the interaction of endogenous polymeric HA with HABP since, in other systems, oligosaccharides have been shown to have a much lower affinity for cell surface HA receptors than polymer. See Underhill, C. and Toole, B. *J. Cell Biol.*, 82:475–484 (1979); Laurent et al., *Biochem. J.*, 234:653–658 (1986). The interaction of HA oligosaccharide with unoccupied cell surface HABP must stimulate second messenger-generating assemblies within the cell since the HA receptors so far described are transmembrane receptors. The inhibitory effects at high concentration result from loss of the receptor by down-regulation, as discussed above.

There is considerable evidence that the intracellular domain of HA receptors of several cell types is linked to the cytoskeleton and can be phosphorylated. Lacy, B. and Underhill, C. *J. Cell Biol.*, 105:1395–1404 (1987); Turley et al., *Exp. Cell Res.*, 187:243–249 (1990); Lokeshwar, V. and Bourguignon, L. *J. Biol. Chem.*, 266:17983–17989 (1991); Camp et al., *J. Cell Biol.*, 115:1283–1292 (1991); Carter, W. and Wayner, E. *J. Biol. Chem.*, 263:4193–4201 (1988); Kalomiris, E. and Bourguignon, L. *J. Biol. Chem.*, 264:8113–8119 (1989). This evidence suggests that the HA receptors are involved in signal transduction. HA-HABP interactions at the endothelial cell surface are essential to endothelial cell morphogenesis. It has been shown, however, that blood vessels fail to form in HA-enriched tissues in vivo. Feinberg, R. and Beebe, D. *Science*, 220:1177–1179 (1983). This latter phenomenon is due to the inhibition of the proliferative phase of angiogenesis since concentrations of polymeric HA greater than 100 $\mu$g/ml inhibit endothelial cell proliferation in culture and low concentrations do not. See West, D. and Kumar, S. *Exp. Cell Res.*, 1983:179–196 (1989). Thus, the concentration of HA in the extracellular matrix is partly responsible for specifying the sites of angiogenesis or vasculogenesis during embryonic development. Low concentrations of HA would be essential whereas high concentrations would be inhibitory.

Malignant tumors are also enriched in hyaluronan, especially the peritumoral region where tumor cells penetrate normal surroundings tissue. Moreover, the tumor cells stimulate the normal cells to produce hyaluronan in this region. See Biswas, C. and Toole, B. *Cell Membranes* Vol. 3 (ed. Elson et al.) pp 341–363 (1987). In addition, tumor cells in culture express HABP, Nemec, R. et al., *Biochem. Biophysical Res. Comm.*, 149:249–257 (1987), and the IVd4 antigen.

MAb IVd4 As A Therapeutic Agent

The antibodies which specifically bind to HABPs can be used in different forms of therapy for treatment of tumors. In a preferred embodiment, MAb IVd4, a fragment thereof, or another monoclonal antibody which specifically binds to HABP, can be used to passively inhibit growth of a tumor by inhibiting angiogenesis. In passive immunotherapy, an effective anti-tumor amount of the monoclonal antibody is administered in a physiologically acceptable carrier to a mammal afflicted with a tumor. The monoclonal antibody inhibits angiogenesis by specifically binding to HABP, and thereby blocking the interaction of endogenous hyaluronan with HABP.

An effective anti-tumor amount quantity the monoclonal antibody (e.g., MAb IVd4) is that quantity which will inhibit endothelial cell proliferation. The actual quantity given in a specific case will vary according to the method of administration and the clinical needs of the patient.

A monoclonal antibody, or fragment thereof, which specifically binds to HABPs can be used as a treatment for a mammal affected with a metastatic tumor. An effective anti-metastatic quantity of the monoclonal antibody is administered in a physiologically acceptable carrier to a mammal afflicted with a metastatic tumor. The monoclonal antibody inhibits tumor cell migration by specifically binding to, or reacting with, HABP, and thereby blocking the interaction of endogenous hyaluronan with HABP.

An effective anti-metastatic quantity of the monoclonal antibody is that quantity which will inhibit tumor cell migration. The actual quantity given in a specific case will vary according to the method of administration and the clinical needs of the patient.

Acceptable physiological carriers are those which dissolve the monoclonal antibody or hold it in suspension, and which are compatible with physiological conditions. Examples of acceptable carriers are aqueous solutions of salts or non-ionic compounds such as sodium chloride or glucose, generally at an isotonic concentration. Those skilled in the art will know, or will he able to ascertain with no more than routine experimentation, particular physiological carriers for the monoclonal antibody composition.

The monoclonal antibody composition will be administered into a vein, artery or into the spinal fluid over the course of from about 2 minutes to about 45 minutes, preferably from 10 to 20 minutes. Where the tumor is supplied by a known artery, intraarterial administration is preferred. Intradermal and intracavity administration are advantageous for tumors restricted to areas close to particular regions of the skin and/or particular body cavities.

The monoclonal antibody composition can also be directly introduced into a surgical site from which a tumor has been removed. The introduction of the monoclonal antibody will inhibit the reemergence of the tumor by inhibiting endothelial cell proliferation. If a metastatic tumor has been removed, the introduction of the monoclonal antibody will inhibit the migration of any tumor cells which were inadvertently left behind. The therapeutic composition can be introduced into the surgical site by injection, perfusion or direct application of a biocompatible gel, film or sponge containing the monoclonal antibody composition. When directly introduced into a surgical site, the dosage is generally about 25 $\mu$g/ml to about 500 $\mu$g/ml. The dosage will vary, however, depending on the individual, the disease type, the disease state, the method of administration and other clinical variables.

In another embodiment, a monoclonal antibody, or a fragment thereof, which specifically binds to HABPs can also be used as a targeting agent to deliver anticancer agents selectively to endothelial cells that vascularize a tumor. Various pharmaceutical or cytotoxic agents can be covalently or noncovalently coupled to the antibodies to form an antibody conjugate. Examples of useful therapeutic agents include: radioactive compounds (e.g., 1251, 1311); agents which bind DNA, such as alkylating agents or various antibiotics (e.g., daunomycin, adriamycin, chlorambucil); anti-metabolites (e.g., methotrexate); and inhibitors of protein synthesis (e.g., diphtheria toxin and toxic plant proteins); cytokines (e.g., tumor necrosis factor, interferon and interleukin 2. Methods of forming these conjugates are known in the art. See, e.g., Rodwell et al., U.S. Pat. No. 4,671,958.

Antibodies which specifically bind to HABPs also can be used to target human effector cells (e.g., macrophages, cytotoxic T cells) against tumor cells. For this purpose bifunctional antibodies can be produced which have an anti-HABP specificity and an anti-effector cell specificity. For example, an anti HABP antibody (or an antigen binding region derived from an anti-HABP antibody) can be coupled to an antibody against $F_c$ receptor of a human effector cell. The conjugate so formed can be used to arm an effector cell. The effector cells either lyse or phagocytose the target cells, depending upon the effector cell type, the target cell type and the specific $F_c$ receptor type involved. The conjugate so formed can be used to arm an effector cell which expresses $F_c$ receptor. Monoclonal antibodies which are specific for the $F_c$ receptor of human effector cells are described by Anderson, et al. in U.S. Pat. No. 4,954,617, the teachings of which are incorporated herein by reference. See also Anderson, C. et al., *J. Biol. Chem.* (1986). The antibodies described in that patent are particularly useful antibodies for effector cell targeting because the binding of these antibodies to effector cells is not blocked by physiological concentrations of IgG. For example, the anti-HABP antibody MAb IVd4 can be coupled to one of the Anderson antibodies to form a heteroantibody which can be bound to a human macrophage to target the macrophage for cancerous tumors.

When the antibodies are used as targeting agents they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal or intracavity administration is advantageous. In addition, intrathecal administrations may be used for tumors located in the brain. Intradermal and intracavitary administration are advantageous for tumors restricted to areas close to particular regions of the skin and/or to particular body cavities.

A typical injectable composition contains about 10 mg human serum albumin (1% USP, Parke-Davis) and from about 20 to 200 micrograms of antibody per milliliter of 0.01M phosphate buffer (pH 7.5) containing 0.9% NaCi.

Oligosaccharide As A Therapeutic Agent

In another embodiment of this invention, HA oligosaccharides are used for the treatment of a mammal afflicted with a tumor. An effective antitumor amount of an HA oligosaccharide is admixed with a physiologically acceptable carrier to form a composition which can be administered by an intravenous, intraarterial or intrathecal injection. As described above, high concentrations of HA oligosaccharides lead to a reduction in the level of membrane-associated HABPs and a corresponding reduction in HA-HABP interactions. As a result, endothelial cell motility and capillary-like tubule formation is inhibited.

The HA oligosaccharides that are preferred for use in therapeutic applications are those having between one disaccharide unit and 16 repeating disaccharide units. It is even more preferable to use HA oligosaccharides having between three repeating units (hexasaccharide) and seven repeating disaccharide units (tetradecasaccharide).

An effective anti-tumor quantity of an HA oligosaccharide is that quantity which will inhibit the formation of capillary-like tubules. The actual quantity given in a specific case will vary according to the method of administration and the clinical needs of the patient.

HA oligosaccharides can also be used as a treatment for a mammal afflicted with a metastatic tumor. An effective anti-metastatic quantity of an HA oligosaccharide is administered in a physiologically acceptable carrier to a mammal afflicted with a metastatic tumor. The HA oligosaccharide inhibits tumor cell migration by specifically binding to, or reacting with, HABP, and thereby blocking the interaction of endogenous hyaluronan with HABP.

An effective anti-metastatic quantity of a HA oligosaccharide is that quantity which will inhibit tumor cell migration. The actual quantity given in a specific case will vary according to the method of administration and the clinical needs of the patient.

Acceptable physiological carriers are those which dissolve the HA oligosaccharide or hold it in suspension, and which are compatible with physiological conditions. Examples of acceptable carriers are aqueous solutions of salt or non-ionic compounds such as sodium chloride or glucose, generally at an isotonic concentration. Other drugs or agents may be present in the solution with the HA oligosaccharide so long as the additional components do not interfere with the ability of the HA oligosaccharide to inhibit tumor proliferation. Those skilled in the art will know, or will be able to ascertain with no more than routine experimentation, particular physiological carriers for an HA oligosaccharide composition.

The HA oligosaccharide composition will be administered into a vein, artery or the spinal fluid over the course of from about 2 minutes to about 45 minutes, preferably from 10 to 20 minutes. Where the tumor is supplied by a known artery, intraarterial administration is preferred. Intradermal and intracavity administration are advantageous for tumors restricted to areas close to particular regions of the skin and/or particular body cavities. The injections can be repeated as necessary to inhibit the proliferation of the tumor.

An HA oligosaccharide composition can also be directly introduced into a surgical site from which a tumor has been removed. The introduction of HA oligosaccharide composition into a surgical site will inhibit blood vessel formation and, therefore, the reemergence of the tumor. If a metastatic tumor has been removed, the introduction of the HA oligosaccharide will inhibit the migration of any tumor cells which were inadvertently left behind. The therapeutic composition can be introduced into the surgical site by injection, perfusion or direct application of a biocompatible gel, film or sponge containing the HA oligosaccharide composition. When directly introduced into a surgical site the appropriate dosage is generally about 50 $\mu$g/ml to 5 mg/ml. The dosage will vary, however, depending on the individual, the disease type, the disease state, the method of administration and other clinical variables.

An HA oligosaccharide can also be used as a targeting agent to deliver anti-cancer agents selectively to endothelial cells that vascularize a tumor. Various pharmaceutical or cytotoxic agents can be covalently or noncovalently coupled to an HA oligosaccharide to form an oligosaccharide conjugate. Examples of useful therapeutic agents include: radioactive compounds (e.g., 125I, 131I); agents which bind DNA, such as alkylating agents or various antibiotics (e.g., daunomycin, adriamycin, chlorambucil); anti-metabolites (e.g., methotrexate); inhibitors of protein synthesis (e.g., diphtheria toxin and toxic plant proteins); and cytokines (e.g., tumor necrosis factor, interferon and interleukin 2. Those skilled in the art will know, or be able to determine without undue experimentation, methods of forming these conjugates.

When HA oligosaccharides are used as targeting agents they are preferably administered in the form of injectable compositions. The injectable oligosaccharide solution will be administered into a vein, artery or into the spinal fluid over the course of from 2 minutes to about 45 minutes, preferably from 10 to 20 minutes. In certain cases, intradermal or intracavity administration is advantageous. In addition, intrathecal administrations may be used for tumors located in the brain. Intradermal and intracavitary administration are advantageous for tumors restricted to areas close to particular regions of the skin and/or to particular body cavities.

MAb IVd4 and HA Oligosaccharides As Therapeutic Agents In Other Angiogenic Disease States The HABP-specific monoclonal antibodies and the HA oligosaccharides can be used to treat diabetic retinopathy. Diabetic retinopathy, which is characterized by a proliferation in the endothelial cells in the retina of the eye, is commonly associated with diabetes mellitus and is a major cause of irreversible blindness. See Tolentino, F. and Cajita, V. *Annals Academy of Medicine* 18:204–213 (1989).

Diabetic retinopathy is the result of the eye's effort to repair damage resulting from compromised metabolic, endocrine and hematologic systems. Tolentino and Cajita postulate that damaged retinal blood vessels produce retinal ischemia, which in turn injures the retina and marshalls all the tissue processes of repair. It is believed that angiogenic factor(s) stimulate vessel formation to satisfy the ischemic tissues' demand for oxygen and other metabolites.

An effective anti-angiogenic amount of an HA oligosaccharide or monoclonal antibody is admixed with a physiologically-acceptable carrier to form a therapeutic composition which can be administered by injection. (Acceptable physiologically carrier have been described previously.) The therapeutic composition may be administered into a blood vessel or directly into the eye itself.

MAb IVd4 As A Diagnostic Agent

MAb IVd4, or other monoclonal antibodies that specifically bind to HABP, can be used for the diagnosis of tumors by in vivo tumor imaging techniques. An antibody specific for HABP, or preferably an antigen binding fragment thereof, is conjugated to a label (e.g., a gamma emitting radioisotope) which generates a detectable signal and administered to a mammal suspected of having a tumor. After sufficient time to allow the detectably-labeled antibody to localize at the tumor site (or sites), the signal generated by the label is detected by a photoscanning device. The detected signal is then converted to an image of the tumor. This image makes it possible to localize the tumor in vivo. This data can then be used to develop an appropriate therapeutic strategy.

Antibody fragments, rather than whole antibody molecules, are generally preferred for use in tumor imaging. Antibody fragments accumulate at the tumor(s) more rapidly because they are distributed more readily in the tissues than are entire antibody molecules. Thus an image can be obtained in less time than is possible using whole antibody. These fragments are also cleared more rapidly from tissues, resulting in a lower background signal. See, e.g., Haber et al., U.S. Pat. No. 4,036,945; Goldenberg et al., U.S. Pat. No. 4,331,647. The divalent antigen binding fragment (Fab')$_2$ and the monovalent Fab are especially preferred. Such fragments can be prepared by digestion of the whole immunoglobulin molecule with the enzymes pepsin or papain according to any of several well known protocols. The types of labels that are suitable for conjugation to a monoclonal antibody for tumor localization include, but are not limited to radiolabels (i.e., radioisotopes), fluorescent labels and biotin labels.

Among the radioisotopes that can be used to label antibodies or antibody fragments, gamma emitters, positron-emitters, X-ray-emitters and fluorescence-emitters are suitable for localization. Suitable radioisotopes for labeling antibodies include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

The gamma-emitters Indium-111 and Technetium-99m are preferred because these radiometals are detectable with a gamma camera and have favorable half lives for imaging in vivo. Antibody can be labelled with Indium-111 or Technetium-99m via a conjugated metal chelator, such as DTPA (diethlenetriaminepentaacetic acid). See Krejcarek et al., *Biochem. Biophys. Res. Com.*, 77:581 (1977); Khaw, B. A. et al., *Science*, 209:295 (1980); Gansow et al., U.S. Pat. No. 4,472,509; Hnatowich, U.S. Pat. No. 4,479,930, the teachings of which are incorporated herein by reference.

Fluorescent compounds that are suitable for conjugation to a monoclonal antibody include fluorescein sodium, fluorescein isothiocyanate, and Texas Red sulfonyl chloride. See, DeBelder, A. and Wik, K. *Carbohydrate Research*, 44:257–257 (1975). Those skilled in the art will know, or will be able to ascertain with no more than routine experimentation, other fluorescent compounds that are suitable for labeling monoclonal antibodies.

Human tissue specimens (e.g., biopsy samples) can be tested for high expression levels of the HABP by using monclonal antibodies (e.g., MAb IVd4) in an immunohistochemical technique, such as the immunoperoxidase staining procedure. Alternatively, immunofluorescent techniques can be used to examine human tissue specimens. In a typical protocol, slides containing cryostat sections of frozen, unfixed tissue biopsy samples or cytological smears are air dried, and then incubated with the MAb IVd4 antibody preparation in a humidified chamber at room temperature. The slides are layered with a preparation of fluorescently-labelled antibody directed against the monoclonal antibody. The staining pattern and intensities within the sample are determined by fluorescent light microscopy.

Oligosaccharide As A Diagnostic Agent

In yet another embodiment of this invention, HA oligosaccharides can be used for the diagnosis of tumors by in vivo tumor imaging techniques. An HA oligosaccharide is conjugated to a label which generates a detectable signal and administered to a mammal suspected of having a tumor. After sufficient time to allow the detectably-labeled HA oligosaccharide to localize at the tumor site (or sites), the signal generated by the label is detected by a photoscanning device. The detected signal is then converted to an image of the tumor. This image makes it possible to localize the tumor in vivo. This data can be used to develop an appropriate therapeutic strategy.

The HA oligosaccharides that are preferred for use in diagnostic applications are those having between one disaccharide unit and 16 repeating disaccharide units. It is even more preferable to use HA oligosaccharides having between three repeating disaccharide units (hexasaccharide) and seven repeating disaccharide units (tetradecasaccharide).

The types of labels that are suitable for conjugation to an HA oligosaccharide for tumor localization include, but are not limited to radiolabels (i.e., radioisotopes), fluorescent labels, and biotin labels. Methods of generating biotin labelled HA molecules are described in Kongtawelert, P. and Ghosh, P. *Anal. Biochem.* 185: 313–318 (1990).

Radioisotopes that are suitable for labeling oligosaccharides include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m, and Fluorine-18. Isotopic labeling of HA with Iodine-125 is described in Raja, R. et al., *Analytical Biochemistry*, 139:168–177 (1984). The gamma-emitters Indium-111 and Technetium-99m are preferred isotopes for labeling HA oligosaccharides because these radioisotopes are detectable with a gamma camera and have favorable half lives for imaging in vivo.

Fluorescent compounds that are suitable for labeling oligosaccharides include fluorescein sodium, fluorescein isothiocyanate, and Texas Red sulfonyl chloride. See, DeBelder, A. and Wik, K. *Carbohydrate Research*, 44:251–257 (1975). Those skilled in the art will know, or will be able to ascertain with no more than routine experimentation, other fluorescent compounds that are suitable for labeling oligosaccharides.

The invention is illustrated further by the following example.

EXAMPLE

Preparation of HA Hexasaccharide

Hyaluronan (100 mg, Sigma type I or III) was incubated with testicular hyaluronidase (1.8 mg, Sigma type VIII) in 30 ml of 0.05M Na acetate/0.15M NaCi, pH 5.0, at 37° C. for 24 hours. The digests were then boiled and passed over a column of Sephadex G-50 (Pharmacia; 1.5×260 cm; 450 ml total volume) in ammonium acetate buffer, pH 5.0. Each fraction from these columns was assayed for uronic acid and terminal N-acetylhexosamine. Those fractions with a ratio of uronic acid to hexosamine of 2.9 to 3.2 were pooled and rechromatographed on G-50. All fractions from the second column with significant uronic acid and hexosamine content had a ratio of 2.9 to 3.1; the fractions were pooled, reassayed, and found to have a ratio of 3.0.

Preparation of Hyaluronan Binding Proteins

The brains of 12-day chick embryos (about 20 dozen per preparation) were excised and placed in 2.5 volumes of the extraction buffer: 0.3M sucrose/40 mM Tris-HCl, pH 7.4, containing protease inhibitors (purchased from Sigma, St. Louis, Mo.) (2 mM EDTA/1 mM benzamidine HCl/1 mM phenylmethylsulfonyl fluoride/5 mM N-ethylmaleimide/2 mM iodoacetate/0.1 unit/ml aprotinin). The brain tissue was extracted by sonication (Ultrasonic Inc.) with a microtip at a setting of 6–40 for 15 seconds in an ice-water bath. The sonication was repeated 8 to 10 times with cooling between each sonication. The extract was then centrifuged at 700 g for 15 minutes, the supernatant was recentrifuged at 7000 g for 20 minutes, and the supernatant from this step recentrifuged at 140,000 g for 60 minutes. The final supernatant was fractionated by ammonium sulfate precipitation at 20, 40, and 60% saturation. The pellet obtained at 40% saturation was used for further purification of the HABPs.

The 40% ammonium sulfate precipitate was redissolved in the chromatography buffer: 40 mM Tris-HCl, pH 7.4, containing the same protease inhibitor concentrations as in the extraction buffer. The solution was dialyzed against the same buffer and applied to a column of DEAE-cellulose (2.6 cm×7.5 cm) that had been equilibrated in the buffer. The column was washed with 4 column volumes of the buffer and then eluted with 4 column volumes each of 0.22M and 0.5M NaCl in the buffer. The 0.22M NaCl eluate was then applied directly to a column of hyaluronan Sepharose (0.7 cm×15 cm), previously equilibrated with 0.22M NaCl in the same chromatography buffer containing 10 mg/ml 1,2-propanediol (Aldrich Chemicals, Wisconsin). The column was then washed with 10 column volumes of 0.22M NaCl, 8 volumes of 1M NaCl, and 2 volumes of 2M NaCl in buffer, followed by elution with 4M guanidinium HCl in buffer. The final eluate was dialyzed against 0.05M Tris buffer, pH 7.4, and used as antigen for antibody production and screening.

All purification steps were performed at 4° C. Protein concentrations were measured by the Bradford method. See Bradford, N. M. *Anal. Biochem.*, 72:248–254 (1976).

Preparation of Monoclonal Antibodies

The monoclonal antibodies, MAb IVd4 and MAb IIIgl, were produced and characterized according the following procedure.

SJL/J mice were used for injection with the HABP preparation. For the first injection, 200 µg HABP protein was emulsified in complete Freund's adjuvant and the mice were inoculated subcutaneously at several sites. Two boosts of about 50 µg protein in incomplete Freund's were injected approximately, 1 and 2 months later. Another month later, a series of three subcutaneous injections of 50, 75, and 100 µg, respectively, of protein in phosphate-buffered saline were administered 1 day apart. Serum was collected from the mice prior to any injections and subsequent to the first and second boosts. Only mice with antiserum that gave a positive response for HABP antibodies by ELISA, were used for hybridoma production. Preimmune serum was found to be negative in this assay.

Subsequent to the above injections, the mice were sacrificed and their spleens were removed. The splenic lymphocytes were obtained by flushing, washed several times, and fused with a nonsecretor NS-I myeloma variant using polyethylene glycol 1300–1600 (Sigma). The cells were then plated in 96-well Costar culture plates and hybridomas were selected in HAT and HT-containing media. See, e.g., Linsenmayer and Hendrix, *Immunochemistry of the Extracellular Matrix* (H. Furthmayr, Ed.) 1:180–198 (1982).

The media from wells showing growth were tested for the presence of putative antibodies to HABPs as described in the section below. Positive cultures were cloned by limiting dilution in 96-well dishes and the media from the wells were again tested for antibody. Those cells yielding a significant antibody titer were recloned. Hybridoma cells were grown in Dulbecco's modified Eagle's medium (4.5 g/liter glucose) containing 10% fetal bovine serum (Hyclone),/2 mM glutamine or, when indicated, in serum-free HB101 medium (Hana Biologics, Berkeley, Calif.), plus antibiotics. Antibody-containing media were harvested every 7 days and used undiluted for screening. For most other purposes, immunoglobulins were precipitated from the above media with 50% saturated ammonium sulfate at 4° C. for 16 hours. After centrifugation at 10,000 g, the precipitate was dissolved in phosphate buffered saline and dialyzed against the same buffer.

MAb IVd4 recognizes HABP from several cells and tissues, especially embryonic, from a variety of species. MAb IIIgl was prepared from the same series of hybridomas as MAb IVd4 and recognizes an unknown antigert present in the mixed antigen preparation used for immunization of the mice. Both antibodies are of the IgM class.

Assays of HABP Antibodies

The assays for detection of antibodies to HABPs consisted of an ELISA and a two-part dot-blot immunoassay. For ELISA, Immunolon plates (Dynatek Lab, Virginia) were absorbed with HABP (1.25 µg/ml) at 4° C. overnight, washed with 0.1% BSA in phosphate-buffered saline, reacted with hybridoma medium for 60 minutes at room temperature, washed against with 0.1% BSA/phosphate-buffered saline contained 0.1% Tween (Janssen Life Sciences, Piscataway, N.J.), and reacted with biotinylated horse anti-mouse IgG. Final reactions were performed using a Vectastain ABC kit (Vector Labs, California).

For the first part of the dot-blot assay, the HABP preparation (1.25 µg protein/ml) was absorbed onto nitrocellulose (presoaked in 0.1% BSA) in a dotblot apparatus (Bio-Rad), then reacted with hybridoma medium, or Ig isolated from hybridoma medium, for 1 hr and washed with 0.05M Tris/0.15M NaCl, pH 8.0, containing 0.1% Tween. The blots were then reacted with biotinyiated horse anti-mouse IgG, followed by staining using a Vectastain ABC kit. In the second part of the assay, cultures that were positive in the above test were assayed again, in this case after preincubation of the HABP preparation for 16 hr at 4° C. in the presences and absence of 200 µg/ml of hyaluronan prior to absorption to the nitrocellulose.

Endothelial Cell Culture

Endothelial cells were obtained from three sources. Bovine aortic endothelial cells were isolated from aortas collected fresh from a local slaughterhouse and used between passage 4 and 10. Yannariello-Brown et al., *J. Cell Biol.*, 106:1773–1786 (1988). Bovine pulmonary artery cells were from the ATCC (CCL 209) and were used between passage 16 and 30. The cells were maintained in 75 cm$^2$ tissue culture flasks in Dulbecco's Modified Eagle's Medium containing 5% calf serum (aortic endothelium) or Minimum Essential Medium with 20% fetal bovine serum (pulmonary artery endothelium) plus antibiotic/antimycotics. Additional experiments were performed with rat testicular fatpad microvascular endothelium. The cultures were routinely monitored with antibodies to the LDL receptor or Factor VIII, and for acquisition of cobblestone morphology at confluence. For experiments, the cells were harvested in 0.6 mM Versene in phosphate-buffered saline at 37° C., transferred to 35 mm dishes, and allowed to attach in the same media as above.

Sparse cultures are defined as cultures containing approximately 5×10$^4$ cells per 35 mm dish, in which cell contact is rare. Confluent cultures were used 3–4 days beyond the time when they first appeared confluent by microscopic observation, and contained approximately 2×10$^6$ cells per dish.

Wounded Cultures

Confluent cultures of large vessel and microvascular endothelium were used for establishment of "wounded" cultures by a modification of previously published techniques. See, e.g., Sato, Y. and Rifkin, D. *J. Cell Biol.*, 107:1199–1205 (1988); Hoock et al., *J. Cell Biol.*, 112:653–664 (1991). Prior to wounding, the cells were washed extensively with serum-free Dulbecco's Modified Eagle's Medium (aortic) or Minimum Essential Medium (pulmonary) containing 0.1% bovine serum albumin and incubated at 37° C. in the medium for 2 hours. Following this they were incubated at 4° C. for 30 minutes with or without experimental reagents (i.e., antibody or HA hexasaccharide) and washed again in serum-free medium with 0.1% bovine serum albumin. A scratch was then made in the monolayer using a pasteur pipette tip that had been smoothened by flaming. The monolayer was washed to remove debris and fresh serum-free medium containing 0.1% bovine serum albumin, with or without test substances, was added. The culture was then incubated for 8, 17 or 30 hours at 37° C., and processed for photography and/or immunocytochemistry.

In some cases the cultures were washed, scratched, and incubated for 8 hours before addition of antibody or HA hexasaccharide, and then re-incubated for an additional 17 hours in the presence of the particular reagent. These cultures were then processed for photography and/or immunocytochemistry.

For quantitation of migration of the cells in the wounded cultures, photographs were taken at various time intervals using an ocular grid. The photographs were then analyzed for the number of cells migrating from the wound edge within a defined field.

Capillary-Like Tubule Formation

The culture conditions used for production of capillary-like tubules were modified from a combination of previously published methods. See Madri, J. and Williams, S. *J. Cell Biol.*, 97:153–165 (1983); Madri et al., *J. Cell Biol.*, 106:1375–1384 (1988); Kubota et al., *J. Cell Biol.*, 107:1589–1598 (1988). Type I collagen (2 mg/ml; UBI, Lake Placid, N.Y., or Collaborative Res., Bedford, Mass.) and a mixture of basement membrane proteins (50 µg/ml ECL from UBI) were mixed with Dulbecco's Modified Eagle's Medium (aortic) or Minimum Essential Medium (pulmonary), with or without experimental reagents (i.e., antibody or HA hexasaccharide), at 4° C. Confluent endothelial cells from bovine aorta or pulmonary artery were then harvested by scraping in medium containing 1% bovine serum albumin, washed by centrifugation, incubated with or without the experimental reagents at 4° C. for 30 minutes, and resuspended as clumps while mixing with the collagen-ECL mixture at 4° C. The mixture was allowed to gel at 37° C. for 30 minutes, then diluted with serum-free medium and incubated for 48 hours under culture conditions.

In experiments where recovery subsequent to treatment with antibody or hexasaccharide was examined, the cultures were first incubated for 48 hours in the presence of the reagent as described above. They were then incubated in three changes of reagent-free medium containing 2% bovine serum albumin at 37° C. for 15 minutes, and reincubated in the absence of reagent for a further 48 hours.

Immunocytochemistry

The cultures were examined for localization of HABP with MAb IVd4 by routine immunocytochemical methods. Briefly, the cells were washed with phosphate-buffered saline, fixed with 3.7% (w/v) paraformaldehyde in saline for 15 minutes at room temperature, washed, and quenched with 0.1M $NH_4Ci$ or 0.05M glycine in phosphate-buffered saline for 30 minutes. Non-specific reactions were blocked by incubating for 30 minutes with a cocktail containing 10 mg/ml bovine serum albumin, 10 mg/ml dried non-fat milk and 100 µg/ml rabbit IgG. The cells were then washed, incubated with 20 µg/ml primary antibody (MAb IVd4) overnight at 4° C., washed, incubated with 4 µg/ml rhodamine-conjugated rabbit anti-mouse IgG for 30 minutes, washed, and mounted in gel-mount media (Biomedia, California).

RESULTS

Immunocytochemical Localization of HABP

In order to establish the presence in endothelial cells of HABP recognized by MAb IVd4 and to determine whether the localization of HABP is different in motile as compared to sessile cells, sparse, confluent and wounded endothelial cell cultures were examined by immunocytochemistry using MAb IVd4.

Figure 1B:
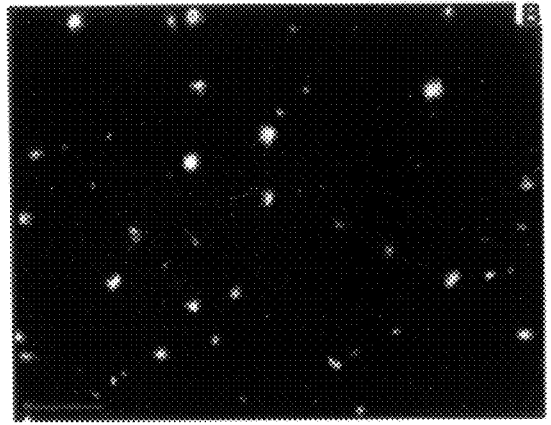
FIG. 1B is a micrograph showing the immunoreactivity of MAb IVd4 with the pulmonary artery endothelial cells shown in FIG. 1A.

FIG. 1A is a micrograph, which was taken under phase contrast, showing a confluent culture of arterial endothelial cells that had not been permeabilized. When this cell culture is incubated with MAb IVd4, immunoreactivity is mainly localized to patches beneath the monolayer, as shown in FIG. 1B. (The bar in FIG. 1B represents 40 µm.)

Figure 2:
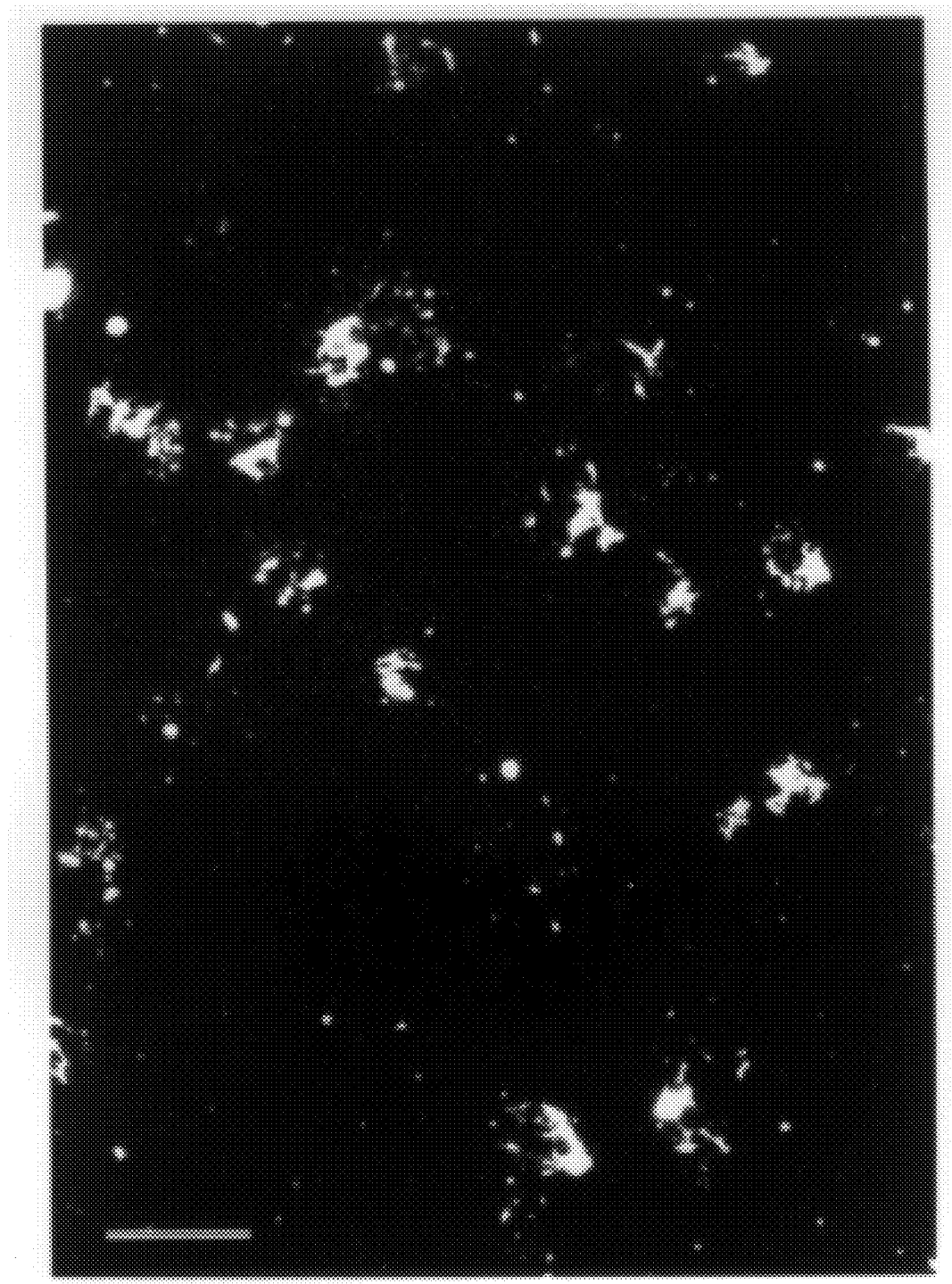
FIG. 2 is a micrograph showing the immunoreactivity of MAb IVd4 with substratum-attached material prepared from a confluent culture.

FIG. 2 is a micrograph showing that after the confluent monolayer of cells is removed with 10 mm EDTA, much of the immunoreactive material remains attached to the substratum. (The bar in FIG. 2 represents 25 µm.) When the cells were permeabilized, strong immunofluorescence was observed within the cytoplasm, mainly in a perinuclear location.

Figure 3A:
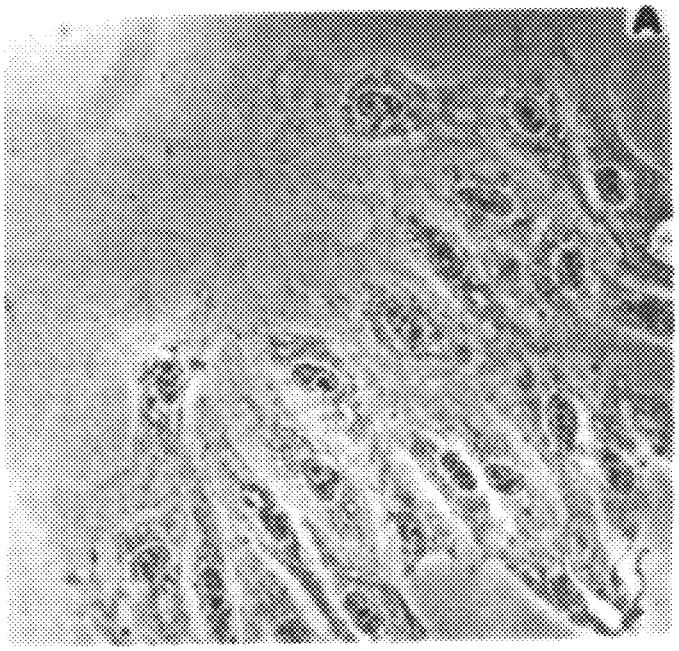
FIGS. 3A and 3C are micrographs showing a wounded monolayer of pulmonary artery endothelial cells under phase contrast.
Figure 3C:
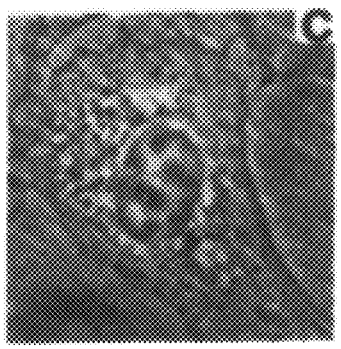
Figure 3B:
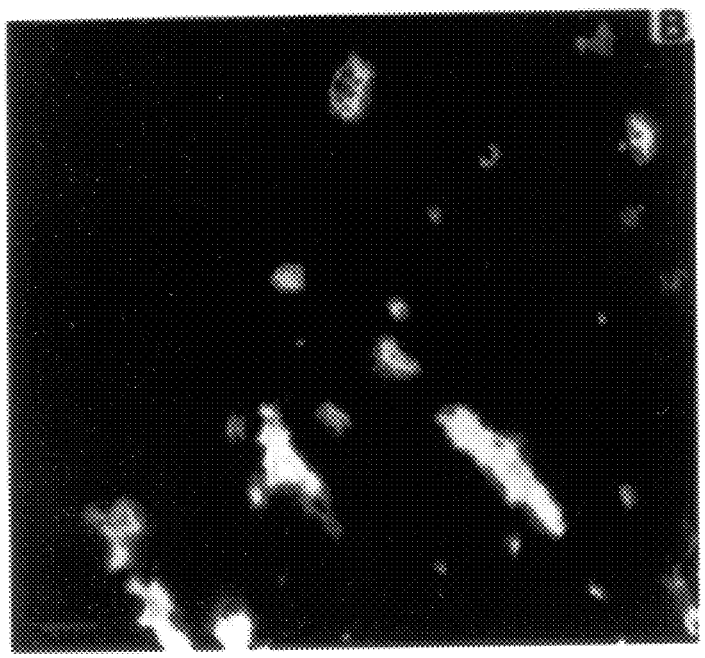
FIGS. 3B and 3D are micrographs showing the immunoreactivity of MAb IVd4 with the endothelial cells shown in FIGS. 3A and 3C, respectively.
Figure 3D:
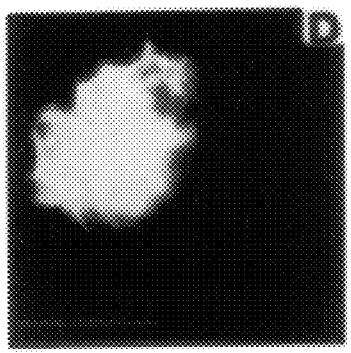

Referring now to FIGS. 3A–3D, it is demonstrated that after endothelial cell cultures are wounded most of the cells emerging from the edges of the confluent monolayer exhibit strong immunoreactivity associated with various regions of their plasma membrane. In approximately 50% of these cells, reactivity was present in lamellipodia at their leading edges. FIG. 3A is a micrograph, taken under phase contrast microscopy, showing a wounded monolayer of pulmonary artery endothelial cells. FIG. 3B is a micrograph showing the immunoreactivity of MAb IVd4 with the wounded monolayer. Immunoreactivity is seen in the cell membranes, including several of the lamellipodia, of the cells emigrating from the edge of the wound. Patches of subcellular reactivity, similar to those seen beneath the cells in non-wounded confluent cultures (FIG. 1), were present in association with the motile cells emerging from the edges of the wounded monolayer as well as the confluent cells remaining behind the edges. When the cells were permeabilized, however, it was apparent that intracellular reactivity was reduced in the motile cells in comparison to the confluent cells behind the wound edges. FIG. 3C is a micrograph showing a cell under phase contrast. FIG. 3D is a micrograph showing the immunoreactivity at the cell's lamellipodium. (The bars represent 18 µm).

A similar pattern of immunoreactivity to the above was seen in sparse, non-wounded cultures of endothelial cells in that many of the cells showed variable regions of membrane staining. These sparse cultures, however, also contained numerous cells that resembled confluent cells in that they only exhibited patches of subcellular reactivity.

The pattern of immunoreactivity was indistinguishable in the bovine aortic and pulmonary artery endothelium. A similar pattern of immunoreactivity to that seen for the bovine aortic and pulmonary artery endothelium was observed in sparse cultures of endothelial cells from human umbilical vein, human aorta, and human omental and rat testicular fatpad microvasculature.

Effect of MAb IVd4 on Endothelial Cell Migration

A series of experiments were conducted to determine whether HA-HABP interactions might be important in endothelial cell migration. Confluent monolayers of bovine aortic endothelial cells were wounded by scratching with a smoothened pasteur pipette. The wounded cells were then incubated for 8 hours (FIGS. 4A and 4B) or 30 hours (FIGS. 4C and 4D) with 280 µg/ml MAb IVd4 (FIG. 4B), 50 µg/ml MAb IVd4 (FIG. 4D) or in the absence of antibody (FIGS.

4A and 4C). (The bars in FIGS. 4A–4D represent 60 μm.) The antibody was found to inhibit emigration of the cells. In particular, 50–100 μg/ml of MAb IVd4 caused partial inhibition, and 250–300 μg/ml of MAb IVd4 caused complete inhibition.

A series of experiments was performed in which concentrations of 50 and 280 μg/ml of MAb IVd4 were added to aortic or pulmonary and rat testicular fatpad artery cells. As can he seen from Table I, the lower concentration of antibody gave rise to an average of 70% inhibition of emigration of the endothelial cells and the higher concentration caused complete inhibition. The results obtained with the aortic endothelium were indistinguishable from those obtained with the pulmonary artery cells and rat testicular fatpad cells. On removal of MAb IVd4 from the cultures subsequent to treatment, the cells initiated migration in similar fashion to controls. Also, addition of 250–500 μg/ml of MAb IIIgl, which is of the same Ig class as MAb IVd4 but does not recognize HABP, had no effect on migration of the endothelial cells.

TABLE I

|  |  | Number of cells migrating per field | |
|---|---|---|---|
|  |  | Mean | S.D. |
| Controls | No MAb | 93.8 | 12.3 |
|  | MAb IIIgl | 96.0 | 5.8 |
| MAb IVd4 | 50 μg/ml | 30.2 | 6.5 |
|  | 280 μg/ml | 0 | 0 |
| Hexa-saccharide | 75 μg/ml | 33.7 | 6.7 |
|  | 500 μg/ml | 0 | 0 |

The effect of MAb IVd4 was also tested on the continuing migration of cells that had already begun to emigrate from the cut edge of the monolayer. When MAb IVd4 was introduced into wounded cultures 8 hours subsequent to wounding, it inhibited further migration of the cells. This illustrates that the effect of MAb IV4 is not only on the initial emergence of the cells.

Effect of HA Oligosaccharides on Endothelial Cell Migration

HA oligosaccharides were tested to determine whether they affect endothelial cell migration because it is known that they (HA oligosaccharides) competitively inhibit interaction of polymeric HA with cell surface HABP. Underhill, C. and Toole, B. *J. Cell Biol.*, 82:475–484 (1979); Underhill et al., *J. biol. Chem.*, 258:8086–8091 (1983). HA hexasaccharide was used because it does not inhibit interaction of HA with link protein or proteoglycans but does inhibit interaction with cell surface HA receptors. Tengblad, A. *Biochem. J.*, 199:297–305 (1981); Yamagata et al., *J. biol. Chem.*, 261:13526–13535 (1986); Nemec et al., *Biochem. Biophys. Res. Comm.*, 149:249–257 (1987).

Referring to FIG. 5, it can be seen that the HA hexasaccharide inhibits the migration of cells in the wounding assay. FIG. 5A is a micrograph showing confluent monolayers of bovine aortic endothelial cells after wounding by scratching with a smoothened pasteur pipette and then incubation in the absence of HA hexasaccharide. FIG. 5B is a micrograph showing confluent monolayers of bovine aortic endothelial cells after wounding by scratching with a smoothened pasteur pipette and then incubation for 8 hours in the presence of 500 μg/ml of HA hexasaccharide. The curved arrows in the margins of the photographs designate the approximate positions of cut edges immediately after wounding. In a dose response, no apparent inhibition was obtained with 25 μg/ml of HA hexasaccharide, partial inhibition was obtained with 50–125 μg/ml, almost complete inhibition was obtained with 300 μg/ml, and complete inhibition with 500 μg/ml. (In FIGS. 5A and 5B, the bar represents 60 μm.) Table I shows that, in a series of experiments performed with both bovine aortic and bovine pulmonary arterial endothelium, 75 μg/ml hexamer gave rise to an average of 66% inhibition and 500 μg/ml totally inhibited emigration. HA tetradecasaccharides (i.e., 14-mer) had similar activity to the hexasaccharide. Similar results were also obtained with rat testicular fatpad cells.

Experiments were also conducted to examine the effect of HA oligosaccharide on MAb IVd4 immunoreactivity. FIG. 6A is a micrograph showing a confluent monolayer of pulmonary artery endothelial cells that were wounded and then incubated in the absence of HA oligosaccharide for 8 hours. The cells immigrated from the wound edges in a manner similar to the cultures shown in FIGS. 3A, 4A and 5A. The culture was then incubated for an additional 17 hours in the presence of 500 μg/ml HA hexasaccharide. The culture was then washed thoroughly with hexasaccharide-free medium, photographed (FIG. 6A), and processed for immunocytochemistry. FIG. 6B is a micrograph showing the immunoreactivity of MAb IVd4 with the endothelial cell culture shown in FIG. 6A. Reactivity was virtually absent in the cell membrane of the treated cells but persisted in the subcellular patches as in FIG. 1B. (The bars in FIGS. 6A and 6B represent 40 μm.) Similar results were obtained with rat testicular fatpad cells. These results indicate that the HA hexasaccharide inhibits endothelial cell migration by causing loss of HABP from the plasma membrane rather than by competition for HA polymer-HABP interaction.

Effect of MAb IVd4 and HA Oligosaccharides on Capillary-Like Tubule Formation

Figures 7A, 7B, 7C, 7D:
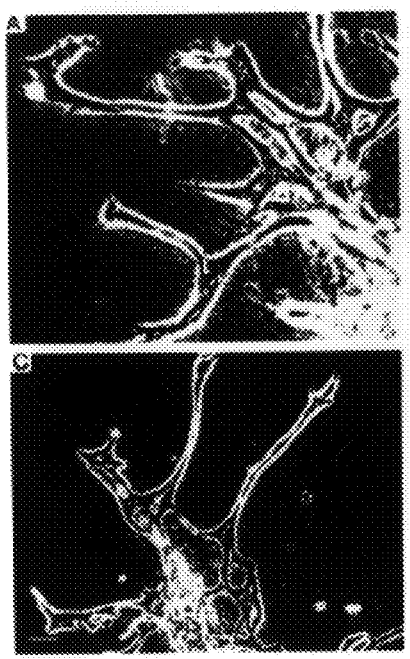
FIG. 7A is a micrograph showing the formation of capillary-like tubules in a pulmonary artery endothelial cell culture.
FIG. 7B is a micrograph showing the inhibition of tubule formation in a pulmonary artery endothelial cell culture after incubation with MAb IVd4.
FIG. 7C is a micrograph showing a pulmonary artery endothelial cell culture after treatment with MAb IVd4 and then incubation in the absence of antibody.
FIG. 7D is an electron micrograph showing one of the capillary-like tubules in a pulmonary artery endothelial cell culture.

A culture system was employed in which endothelial cells grown to confluence in monolayer are transferred into a gel composed of a mixture of type I collagen and basement membrane components. See Madri et al., *J. Cell Biol.*, 106:1375–1384 (1988); Kubota et al., *J. Cell Biol.*, 107:1589–1598 (1988). FIG. 7A is a micrograph showing that in this culture system, the confluent endothelial cells rearrange into capillary-like tubular networks in 24–48 hours. The endothelial cells first form cords in which a partial lumen appears in many locations. As shown in FIG. 7D, these cylindrical vacuoles subsequently fuse to form a longer lumen. FIG. 7D is an electron micrograph of one of the capillary-like tubules within a culture similar to that in FIG. 7A. A continuous basal lamina (arrowheads) surrounding the tubule and tight junctions (straight arrow) between the cells are visible. The lumen of the tubule is clearly apparent between the apical aspects of the endothelial cells. The curved arrow indicates a degenerating endothelial cell in the lumen that did not become incorporated into the tubule wall. (The bar in FIG. 7A represents 60 μm, in FIG. 7D, 1 μm.)

FIG. 7B is a micrograph showing that the addition of 280 μg/ml MAb IVd4 into the gel inhibits tubule formation in an endothelial cell culture. On removal of the antibody, washing of the gel, and reincubation for 48 hours in the absence of antibody, the capillary-like tubules form in similar manner to the controls (FIG. 7C). (In FIGS. 7B and 7C the bar represents 60 μm.)

Figure 8A:
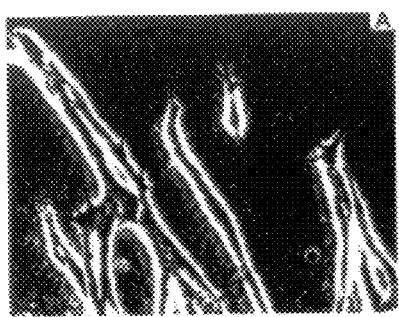
FIG. 8A is a micrograph showing a pulmonary artery endothelial cell culture.
Figure 8B:
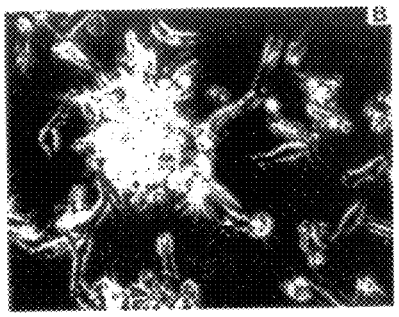
FIGS. 8B and 8C are micrographs showing a pulmonary artery endothelial cell culture after treatment with two different amounts of HA hexasaccharide.
Figure 8C:
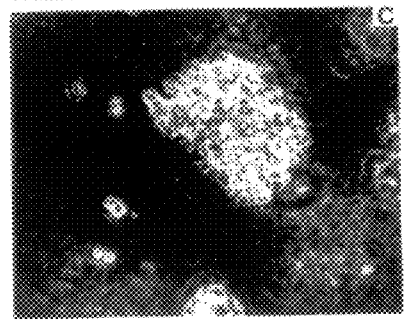
Figure 8D:
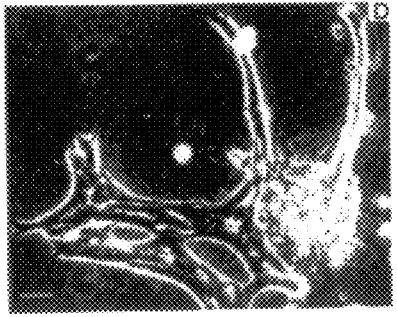
FIG. 8D is a micrograph showing a pulmonary artery endothelial cell culture after treatment with HA hexasaccharide and then incubation in the absence of HA oligosaccharide.

HA oligosaccharides also inhibit capillary-like tubule formation. Pulmonary artery endothelial cells were incubated as described above with respect to FIGS. 7A–7D. FIG. 8A is a micrograph showing a control culture of endothelial cells that were not treated with HA hexasaccharide. FIG. 8B is a micrograph showing that when 75 μg/ml of HA hexasaccharide is added to the cell culture there is a partial inhibition of capillary-like tubule formation. FIG. 8C is a micrograph showing that the addition of 500 μg/ml of HA hexasaccharide causes complete inhibition of capillary-like tubule formation. FIG. 8D is a micrograph showing that tubules formed readily after removal of the HA hexasaccharide, washing of the gel and reincubation for 48 hours in the absence of the hexasaccharide. (The bar in FIG. 8 represents 60 μm.) HA tetradecasaccharides had similar activity to the hexasaccharide.

Bovine aortic and pulmonary arterial endothelial cells responded in similar fashion in the above experiments.

Although the foregoing invention has been described in some detail by way of illustration and example for purposes of clarity of understanding, it will be obvious to one skilled in the art that certain changes and modifications may be practiced within the scope of the appended claims.

Figure 9:
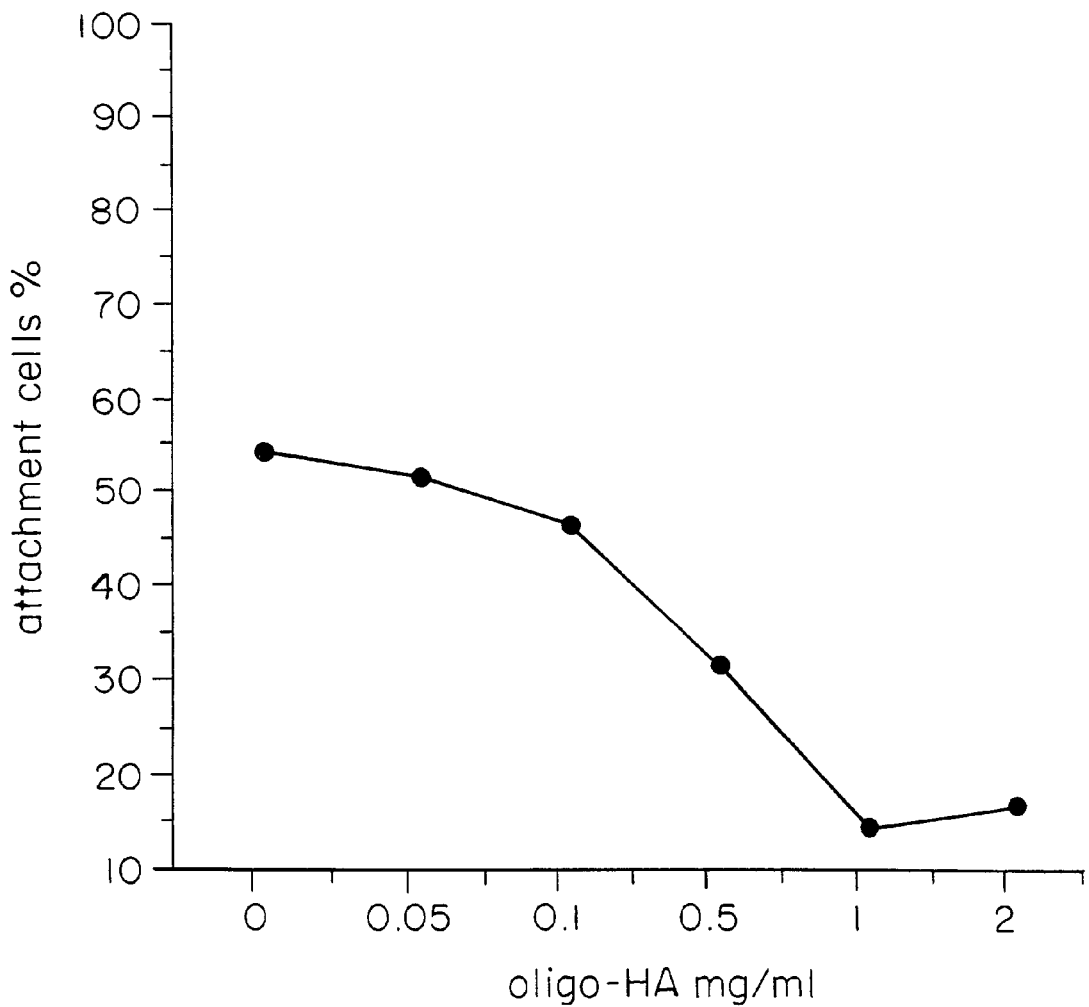
FIG. 9 is a graphic illustration of the inhibition of adhesion of ovarian cancer cells to hyaluronan by hyaluronan oligosaccharides.

S Inhibition of Adhesion of Ovarian Cancer Cells to Hyaluronan by Oligosaccharides of Hyaluronan A suspension of human ovarian cancer cells (SKOV-3) were added to tissue culture wells pre-coated with 5 mg/ml of hyaluronan in the presence or absence of different concentrations of Anika hyaluronan oligosaccharides (SK2-126). The cells were incubated for 30 minutes and then the plates were washed with a measured amount of medium to remove unattached cells. The unattached cells were sedimented by centrifugation, resuspended, counted, and the number of cells remaining attached were calculated. The results, observed visually in the microscope, are shown in FIG. 9. Two other experiments were assessed by microscopic observation and agreed with that given below. An experiment was performed where the cells were first attached to hyaluronan for 15 minutes and subsequently treated with oligomers. In this case the oligomers caused detachment of a large proportion of the cells.

Inhibition of Adhesion of Ovarian Cancer Cells to the Peritoneal Wall Mesentery in vivo by Oligosaccharides of Hyaluronan A suspension of metastatic murine ovarian cancer cells was injected into the peritoneum of mice and the hyaluronan levels at the sites of attachment of these cells to the peritoneal mesentery, the first step in metastasis in ovarian cancer, were examined by specific histochemical staining (Knudson, C. and Toole, B. *J., Cell Biol.,* 100:1753–1758 (1985)). It was found that the hyaluronan concentration became highly elevated at the sites of attachment, confirming in vivo previous evidence showing that tumor cells stimulate hyaluronan production by normal fibroblasts in culture (Knudson, W. et al., *Proc. Nat. Acad. Sci. USA,* 81:6767–6771 (1984)). Based on this finding we hypothesized that hyaluronan oligosaccharides would compete for attachment of the tumor cells to the newly produced hyaluronan and thus reduce or delay the degree of metastasis. Thus the ovarian cancer cells were injected in 200 μl of a solution of 50 mg/ml hyaluronan oligosaccharides (SK2-126) in saline or in 200 μl saline alone. Subsequent to tumor cell injection, the mice were injected twice per day with the oligosaccharides in saline or with saline alone until they were sacrificed at 7 days. The mesentery was removed from two mice injected with tumor cells in the presence of the oligosaccharides and two injected in their absence; they were then washed, fixed and examined for tumor cell attachment by microscopy. Whereas there was extensive attachment of the tumor cells in the absence of oligosaccharides, there was a low amount of attachment in their presence.

Effect of Hyaluronan Oligosaccharides on Tumor Growth

Injection of the 9L glioma intracranially into the rat produces an extremely aggressive brain tumor that typically leads to death of the host within a 2–3 week period. The tumor usually follows a very predictable course of growth. Two experiments have been performed showing a partial delay in tumor-induced death due to administration of hyaluronan (HA) oligomers.

The 9L glioma cells were injected intracranially into Fischer 344 rats, ~200 g in weight (12 experimentals and 12 controls) on day 0. The 12 experimentals were injected intravenously with 0.5 ml saline containing 25 mg/ml HA oligomer (TFT017) once per day from day -2 (2 days prior to tumor injection) until day 15 (15 days after tumor injection). The 12 controls received 0.5 ml saline over the same time course. The experiment was continued without further oligomer or saline injections until all of the animals died. However, this experiment was somewhat complicated by the loss of 3 controls due to accidental drowning.

Figure 10:
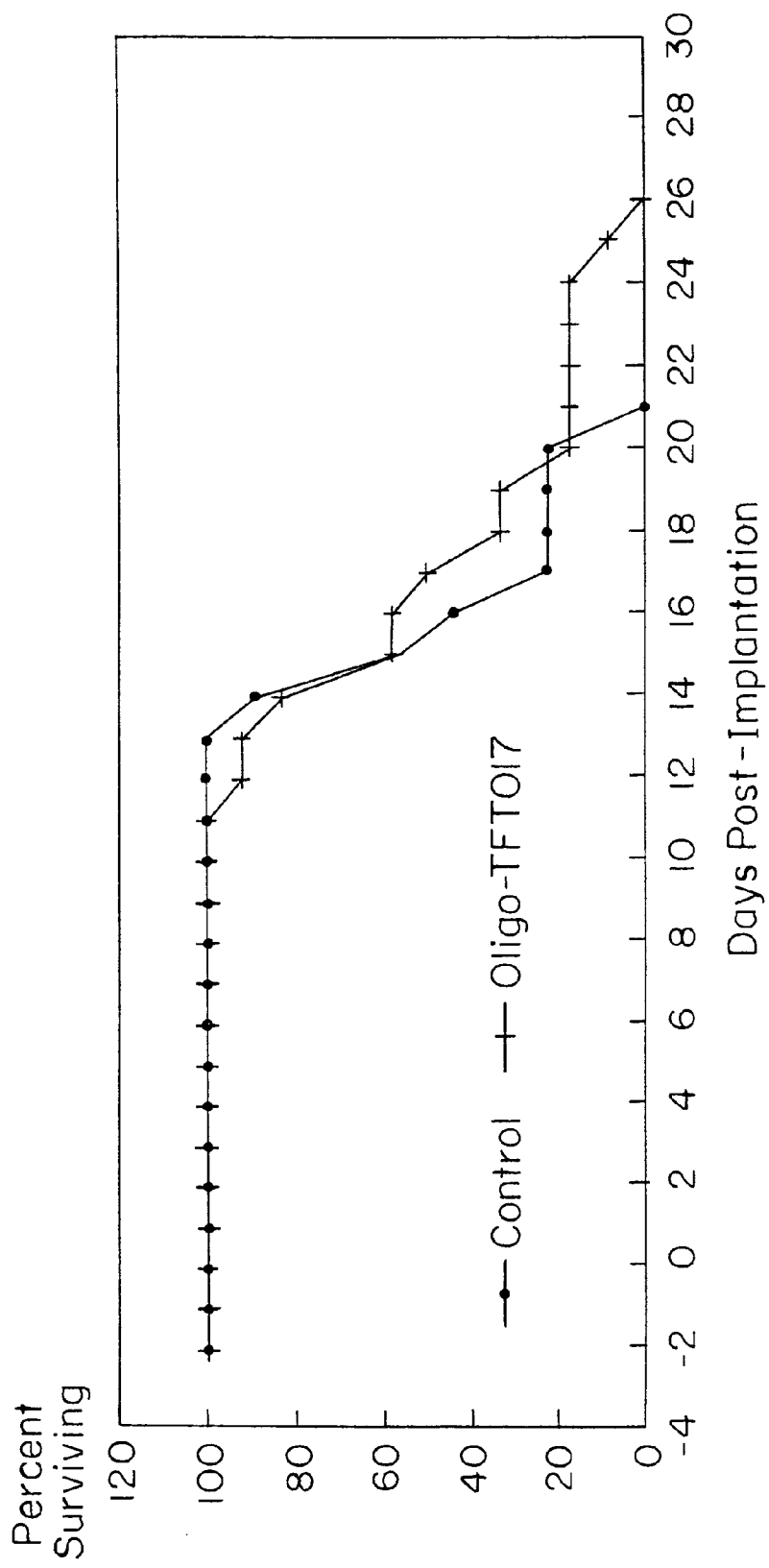
FIGS. 10 and 11 are graphic illustrations of the increased time of survival of rats injected intracranially with 9L glioma cells and treated with hyaluronan oligosaccharides.

The results of the above experiment are shown in FIG. 10; the results are expressed as percent survival of total number of rats at each given time period. A modest delay in onset of death, 2–4 days (~10–20% increased time of survival), occurred in approximately 50% of the animals.

In a second experiment a more aggressive protocol was used. Higher doses of HA oligomer and a longer period of treatment were used. Again, 200 g Fischer 344 rats (in this case 15 experimentals and 15 controls) were injected intracranially with the 9L glioma cells at day 0. The 15 experimentals were injected with 0.4 ml saline containing 300 mg/ml HA oligomer (TFT019) each day from day -2 until day 5. Subsequently, from day 6 until death, each animal was treated with 0.4 ml of 150 mg/ml oligomer per day. The 15 controls were given 0.4 ml saline per day from day -2 until death.

Figure 11:
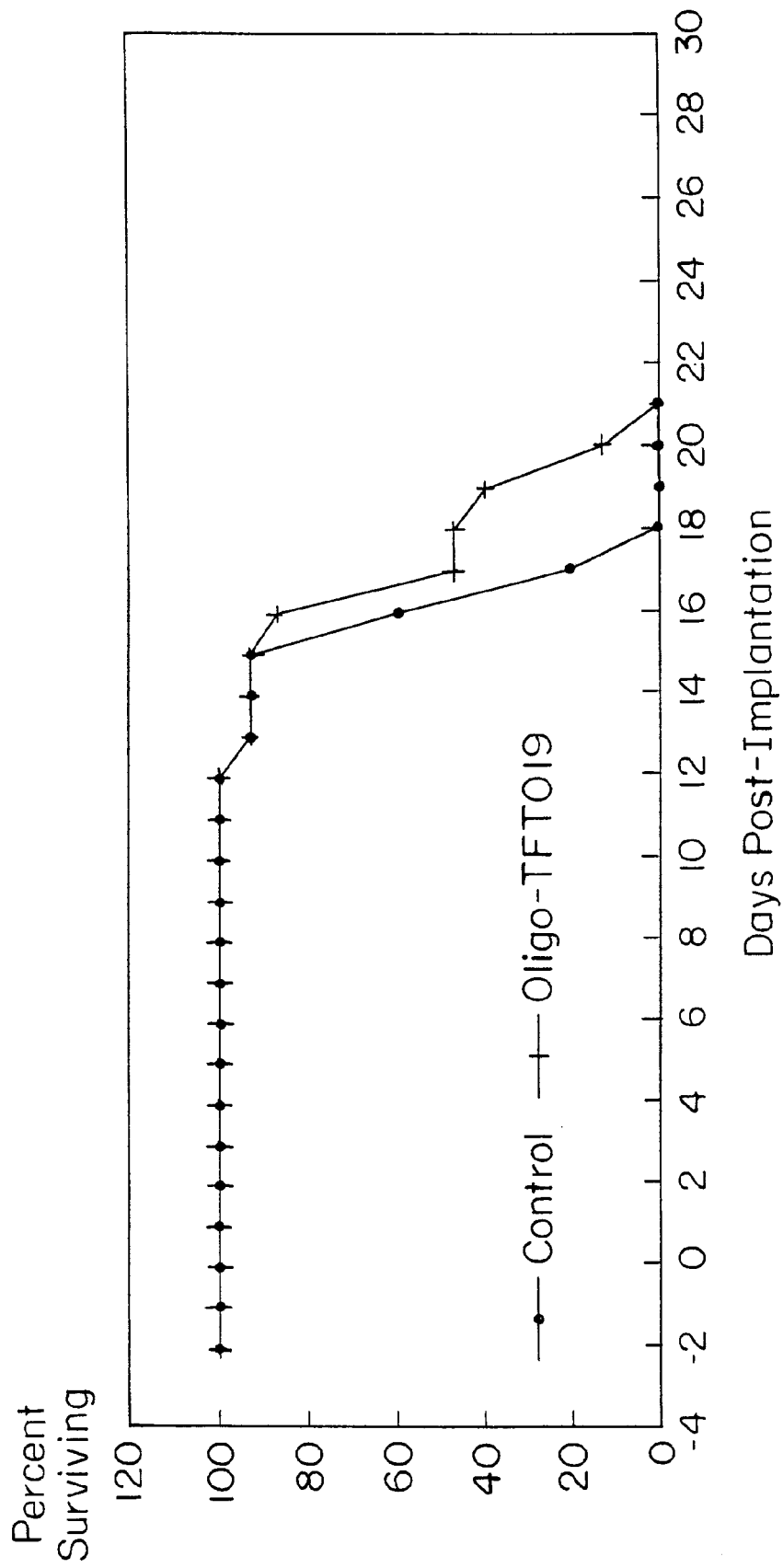

The results of this experiment (see FIG. 11) were very similar to those obtained above. In this experiment, a delay in onset of death of ~3 days (~15–17% increased time of survival) occurred in ~50% of the animals.

The experiments show that the oligomer treatment causes a reproducible increase in survival of the tumor-bearing rats.

ATTC Deposit

The hybridoma cell line which produces monoclonal antibody MAb IVd4 has been deposited with the ATTC, Rockville, Md., and assigned the following accession number: HB 11060.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of inhibiting the growth of a tumor in a mammal, comprising administering an anti-tumor quantity of a hyaluronan oligosaccharide to the mammal having the tumor.

2. The method of claim 1, wherein said oligosaccharide is a tetradecasaccharide.

3. The method of claim 1, wherein said oligosaccharide is a hexasaccharide.

4. A method of inhibiting tumor metastasis in a mammal, comprising administering an anti-metastatic quantity of a hyaluronan oligosaccharide to the mammal having the tumor.

5. The method of claim 4, wherein said oligosaccharide is a tetradecasaccharide.

6. The method of claim 4, wherein said oligosaccharide is a hexasaccharide.

7. A pharmaceutical composition for treating a mammal afflicted with a tumor, comprising a hyaluronan oligosaccharide coupled to a cytotoxic agent.

8. The pharmaceutical composition of claim 7, wherein said hyaluronan oligosaccharide is a tetradecasaccharide.

9. The pharmaceutical composition of claim 7, wherein said cytotoxic agent is methotrexate.

10. The pharmaceutical composition of claim 7, wherein said cytotoxic agent is diphtheria toxin.

11. A pharmaceutical composition for treating a mammal afflicted with a tumor, comprising a hyaluronan oligosaccharide coupled to a cytokine.

12. The pharmaceutical composition of claim 11, wherein said hyaluronan oligosaccharide is a tetradecasaccharide.

13. The pharmaceutical composition of claim 11, wherein said cytokine is selected from the group consisting of tumor necrosis factor, interferon and interleukin 2.

14. A method for treating a mammal afflicted with a tumor, comprising:
    a) excising the tumor from the body site;
    b) administering to the body site where the tumor was excised an anti-tumor quantity of a hyaluronan oligosaccharide.

15. The method of claim 14, wherein said oligosaccharide is a tetradecasaccharide.

16. The method of claim 14, wherein said anti-tumor quantity of said hyaluronan oligosaccharide is from about 50 $\mu$g/ml to about 5 mg/ml.

17. The method of claim 14, wherein said oligosaccharide is a hexasaccharide.

18. A method of inhibiting growth of a tumor in a mammal, comprising administering to the mammal an anti-tumor quantity of a hyaluronan oligosaccharide wherein said oligosaccharide has between 1 and 16 disaccharide units.

19. The method of claim 18, wherein said oligosaccharide has between 3 and 7 disaccharide units.

20. The method of claim 18 wherein said tumor is a glioma or ovarian cancer.

21. A method of inhibiting growth of a tumor in a patient, comprising administering to the patient an anti-tumor quantity of a hyaluronan oligosaccharide.

22. The method of claim 21, wherein said oligosaccharide has between 1 and 16 disaccharide units.

23. The method of claim 21, wherein said oligosaccharide has between 3 and 7 disaccharide units.

24. The method of claim 21, wherein said oligosaccharide is a tetradecasaccharide.

25. The method of claim 21, wherein said oligosaccharide is a hexasaccharide.

26. A method of inhibiting tumor metastasis in a mammal, comprising administering to the mammal an anti-metastatic quantity of a hyaluronan oligosaccharide wherein said oligosaccharide has between 1 and 16 disaccharide units.

27. The method of claim 26, wherein said oligosaccharide has between 3 and 7 disaccharide units.

28. The method of claim 26 wherein said tumor is a glioma or ovarian cancer.

29. A method of inhibiting tumor metastasis in a patient, comprising administering to the patient an anti-metastatic quantity of a hyaluronan oligosaccharide.

30. The method of claim 29, wherein said oligosaccharide has between 1 and 16 disaccharide units.

31. The method of claim 29, wherein said oligosaccharide has between 3 and 7 disaccharide units.

32. The method of claim 29, wherein said oligosaccharide is a tetradecasaccharide.

33. The method of claim 29, wherein said oligosaccharide is a hexasaccharide.

34. A method for treating a mammal with a tumor, comprising:
    a) excising the tumor from the body site;
    b) administering to the mammal an anti-tumor quantity of a hyaluronan oligosaccharide wherein said oligosaccharide has between 1 and 16 disaccharide units.

35. The method of claim 34, wherein said oligosaccharide has between 3 and 7 disaccharide units.

36. The method of claim 34 wherein said tumor is a glioma or ovarian cancer.

37. A method for treating a patient a tumor, comprising:
    a) excising the tumor from the body site;
    b) administering to the patient an anti-tumor quantity of a hyaluronan oligosaccharide.

38. The method of claim 37, wherein said oligosaccharide has between 1 and 16 disaccharide units.

39. The method of claim 37, wherein said oligosaccharide has between 3 and 7 disaccharide units.

40. The method of claim 37, wherein said oligosaccharide is a tetradecasaccharide.

41. The method of claim 37, wherein said oligosaccharide is a hexasaccharide.

* * * * *